(12) United States Patent
Johnson et al.

(10) Patent No.: US 11,564,827 B2
(45) Date of Patent: Jan. 31, 2023

(54) OSTOMY STOMA OUTPUT DIVERSION DEVICE

(71) Applicants: Bruce Johnson, Simpsonville, SC (US); Theresa Johnson, Simpsonville, SC (US); Reed Johnson, Cumming, GA (US)

(72) Inventors: Bruce Johnson, Simpsonville, SC (US); Theresa Johnson, Simpsonville, SC (US); Reed Johnson, Cumming, GA (US)

( * ) Notice: Subject to any disclaimer, the term of this patent is extended or adjusted under 35 U.S.C. 154(b) by 710 days.

(21) Appl. No.: 16/518,506

(22) Filed: Jul. 22, 2019

(65) Prior Publication Data

US 2021/0022912 A1 Jan. 28, 2021

(51) Int. Cl.
*A61F 5/449* (2006.01)
*A61F 5/448* (2006.01)
*A61F 5/44* (2006.01)
*A61F 5/445* (2006.01)

(52) U.S. Cl.
CPC .............. *A61F 5/449* (2013.01); *A61F 5/44* (2013.01); *A61F 5/4404* (2013.01); *A61F 5/445* (2013.01); *A61F 5/448* (2013.01); *A61F 2005/4486* (2013.01)

(58) Field of Classification Search
CPC ........ A61F 5/445; A61F 5/4404; A61F 5/448; A61F 5/449; A61F 5/44
See application file for complete search history.

(56) References Cited

U.S. PATENT DOCUMENTS

| 1,256,857 | A |   | 2/1918  | Wofford |
| 2,314,724 | A |   | 3/1943  | Marsan |
| 2,528,227 | A |   | 10/1950 | Johnson |
| 2,536,036 | A |   | 1/1951  | Cloninger |
| 3,367,338 | A |   | 2/1968  | Crandall |
| 3,577,982 | A |   | 5/1971  | La Par |
| 4,296,749 | A | * | 10/1981 | Pontifex ............... A61F 5/445 604/344 |

(Continued)

FOREIGN PATENT DOCUMENTS

| CN | 107468406 | 12/2017 |
| GB |      5449 | 11/1906 |

(Continued)

*Primary Examiner* — Kai H Weng
(74) *Attorney, Agent, or Firm* — Southeast IP Group LLC; Thomas L. Moses

(57) ABSTRACT

An ostomy output diversion device is used to cover and seal closely around a patient's stoma, to divert stoma effluent output through the device, through a drain tube and into a container or reservoir, temporarily eliminating the need of an adhesive-based ostomy pouching system. The ostomy output diversion device is placed over the person's stoma, with the base ring surrounding the peristomal skin, the adjustable inner tube is retracted until the base ring is centered over the stoma, the body support strap is then placed over the device to secure it to the patient's body, the inner tube with stoma-sized adapter is then extended over the stoma, the patient applies the desired pressure against the skin, then secures the stoma-sized adapter in place with the pressure adjustment lock. The device may also include an ostomy pouch mounting ring for attachment to an ostomy pouch, and a disposable receptacle.

10 Claims, 12 Drawing Sheets

(56) References Cited

U.S. PATENT DOCUMENTS

| | | | | |
|---|---|---|---|---|
| 4,723,952 A | * | 2/1988 | Esposito | A61F 5/448 |
| | | | | 604/338 |
| 5,125,916 A | * | 6/1992 | Panebianco | A61F 5/445 |
| | | | | 604/328 |
| 5,503,625 A | | 4/1996 | Plass | |
| 5,636,643 A | * | 6/1997 | Argenta | A61M 1/0088 |
| | | | | 128/897 |
| 2016/0287428 A1 | * | 10/2016 | Eggert | A61F 5/4405 |
| 2019/0060104 A1 | | 2/2019 | Cesa et al. | |

FOREIGN PATENT DOCUMENTS

| | | |
|---|---|---|
| KR | 20170008000 | 1/2017 |
| WO | WO0100260 A1 | 1/2001 |

* cited by examiner

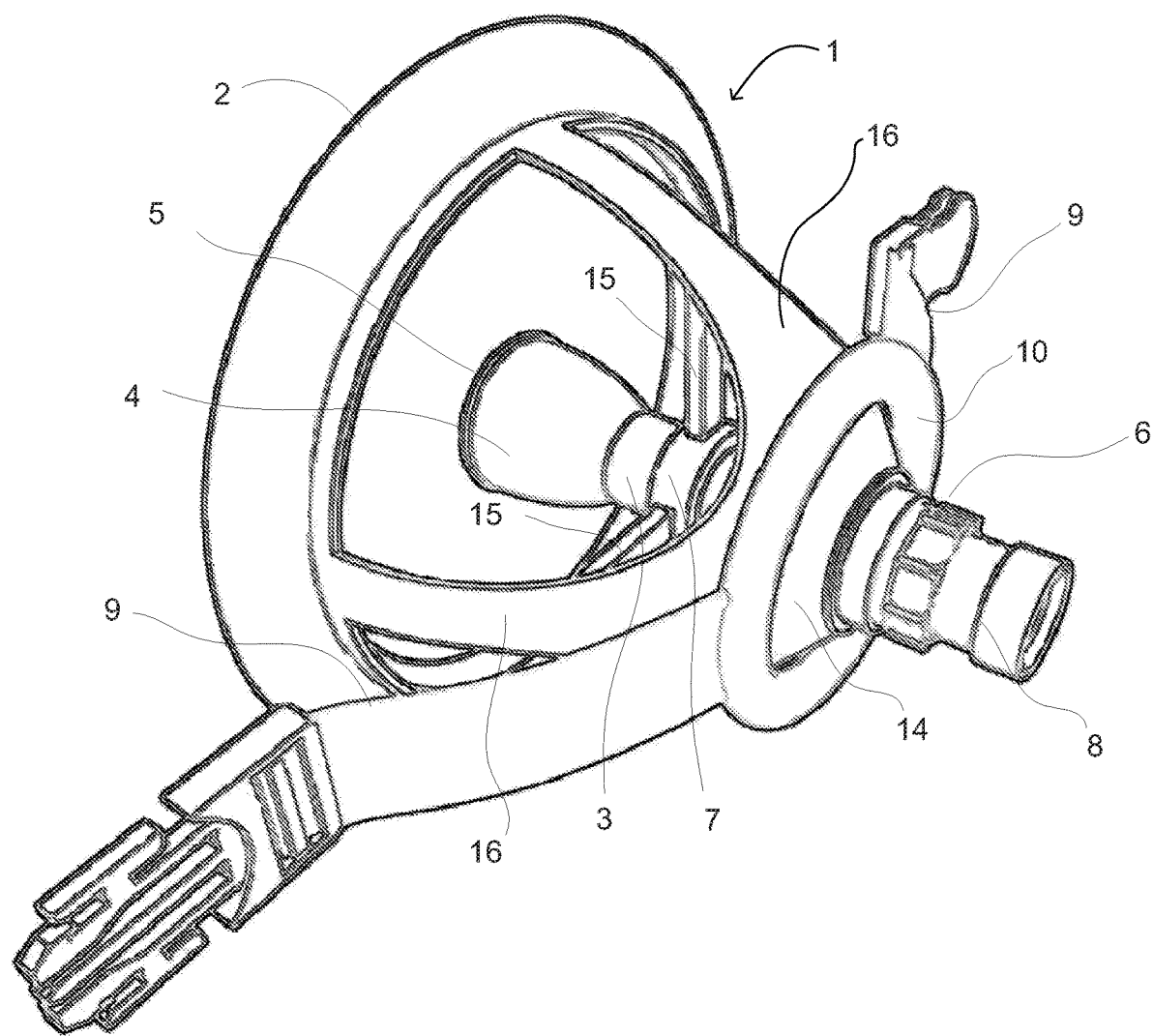
- Fig. 1 -

- Fig. 2 -
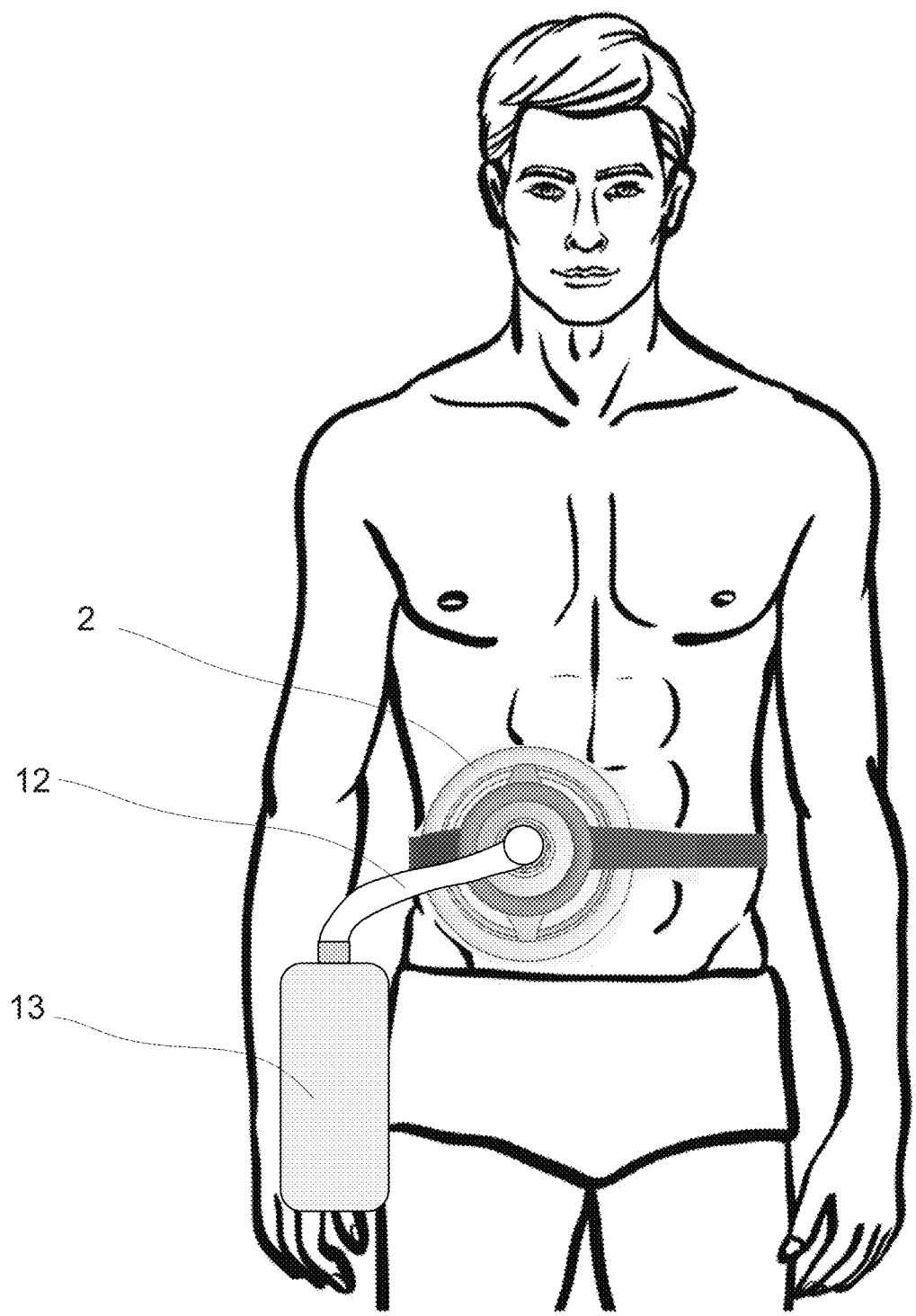

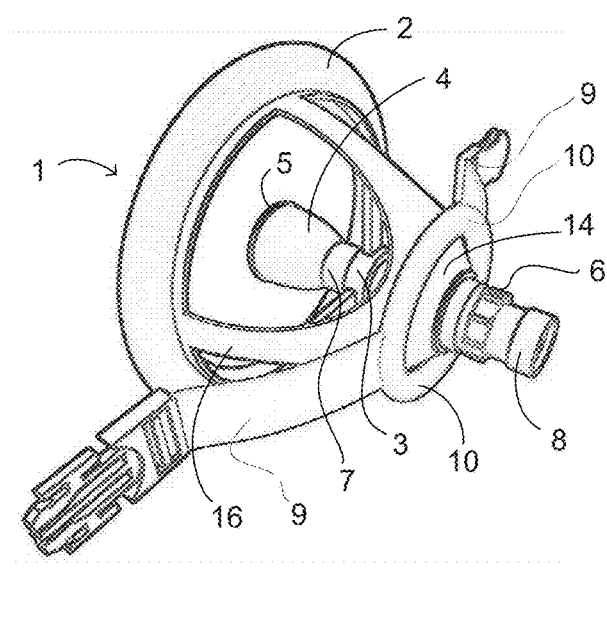
Fig. - 3A -
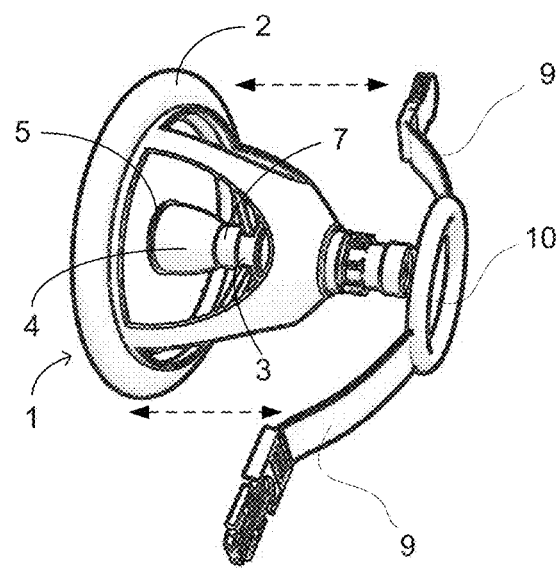
Fig. - 3B -

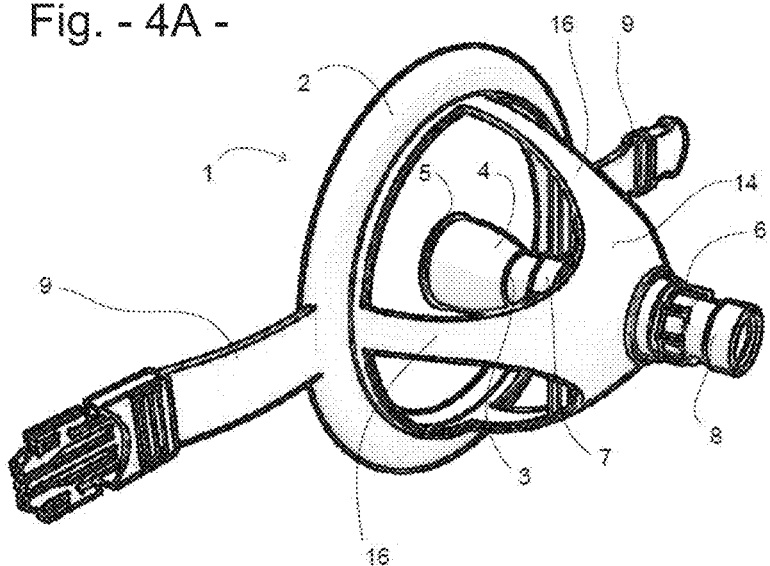
Fig. - 4A -
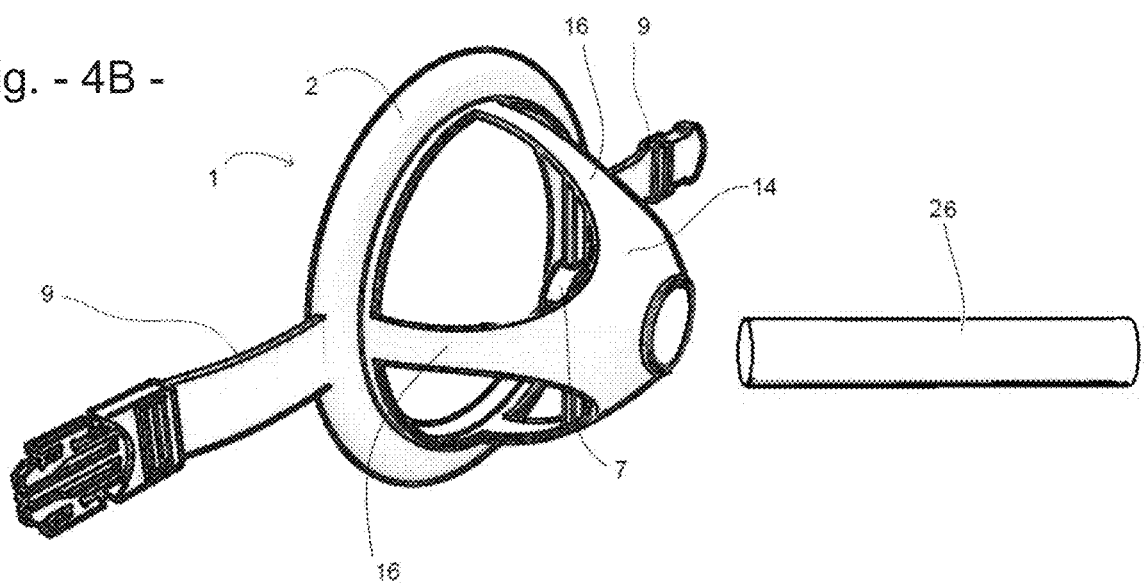
Fig. - 4B -

- Fig. 5 -
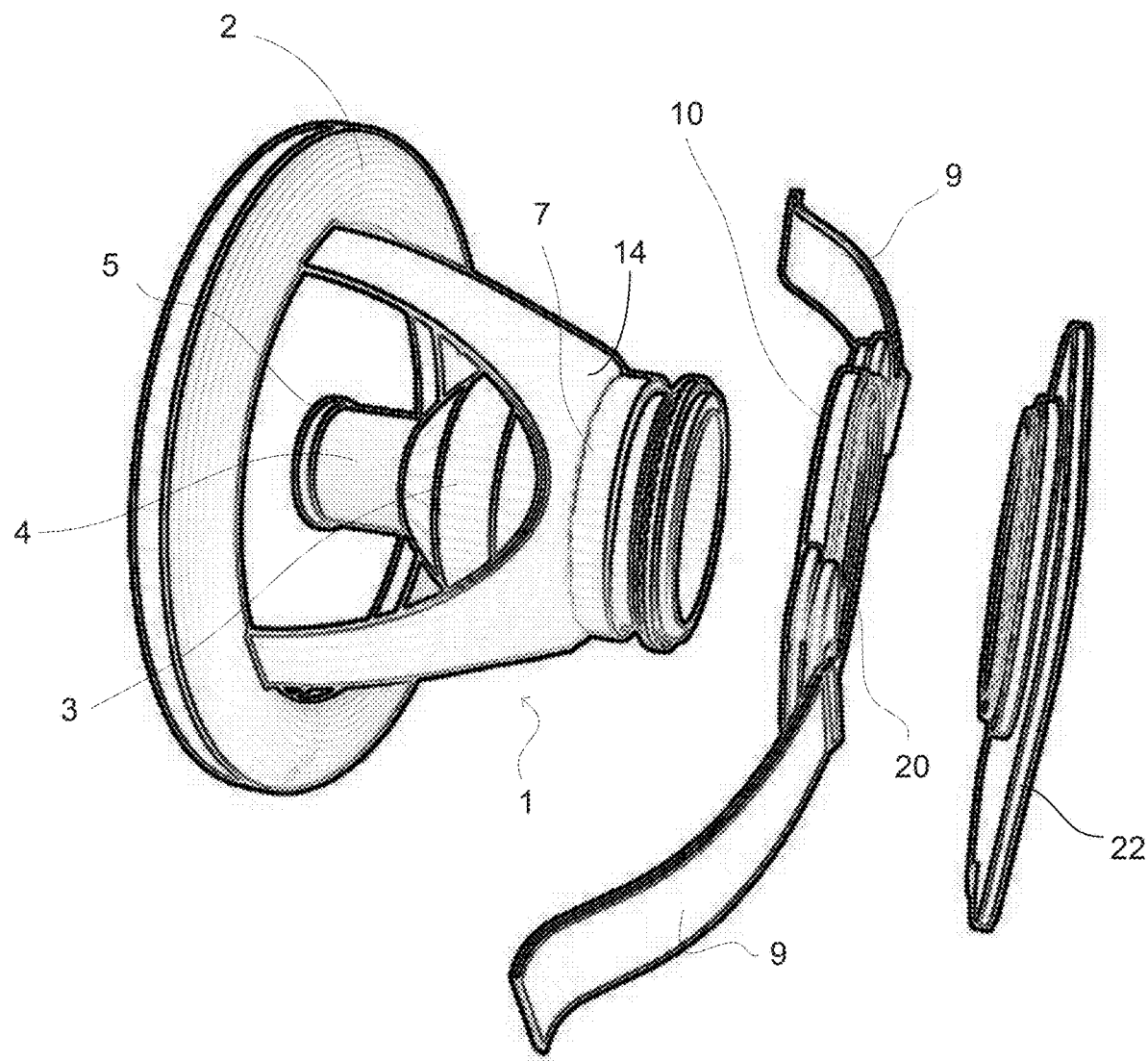

- Fig. 6 -
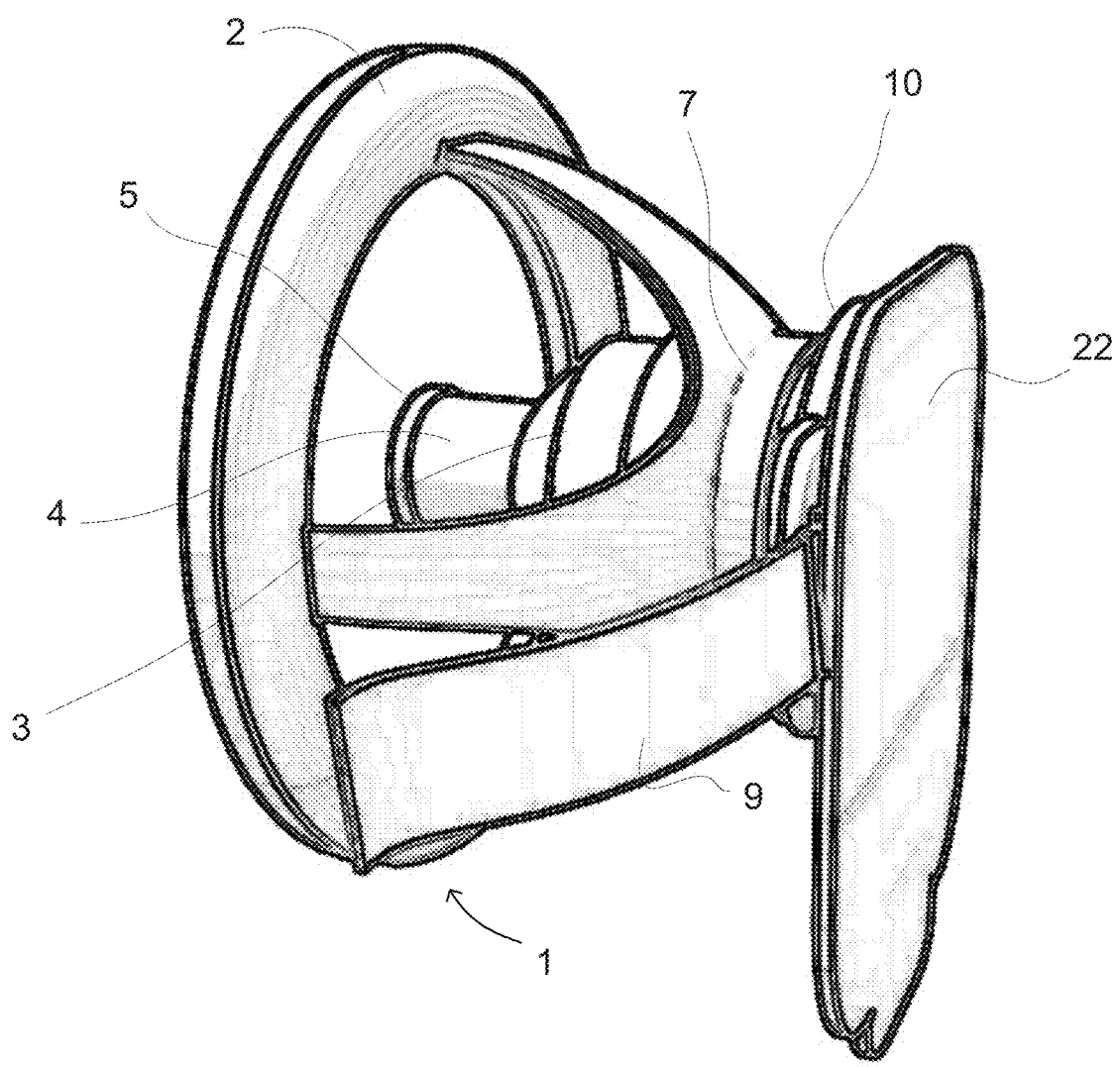

- Fig. 7 -
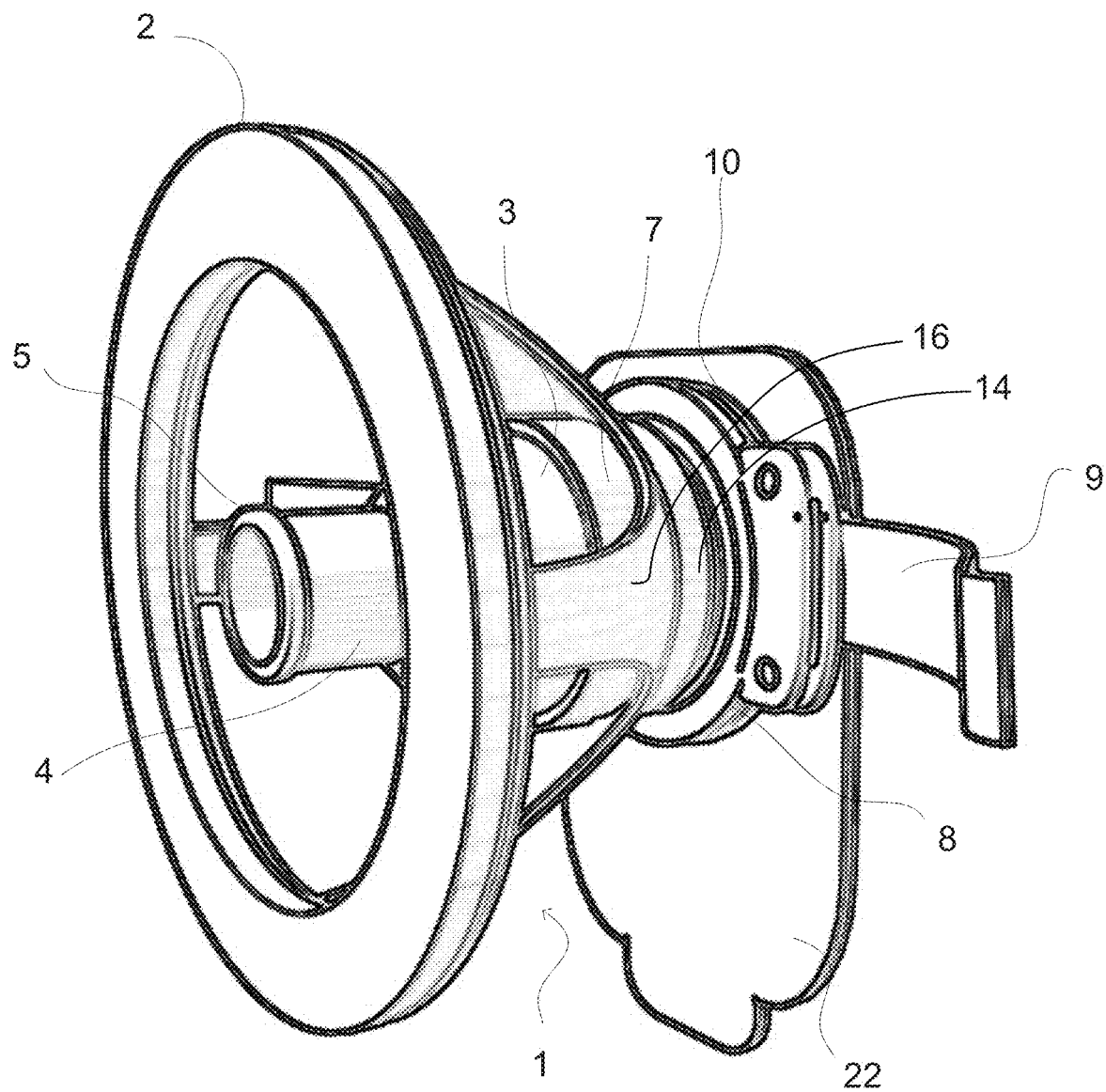

- Fig. 8 -
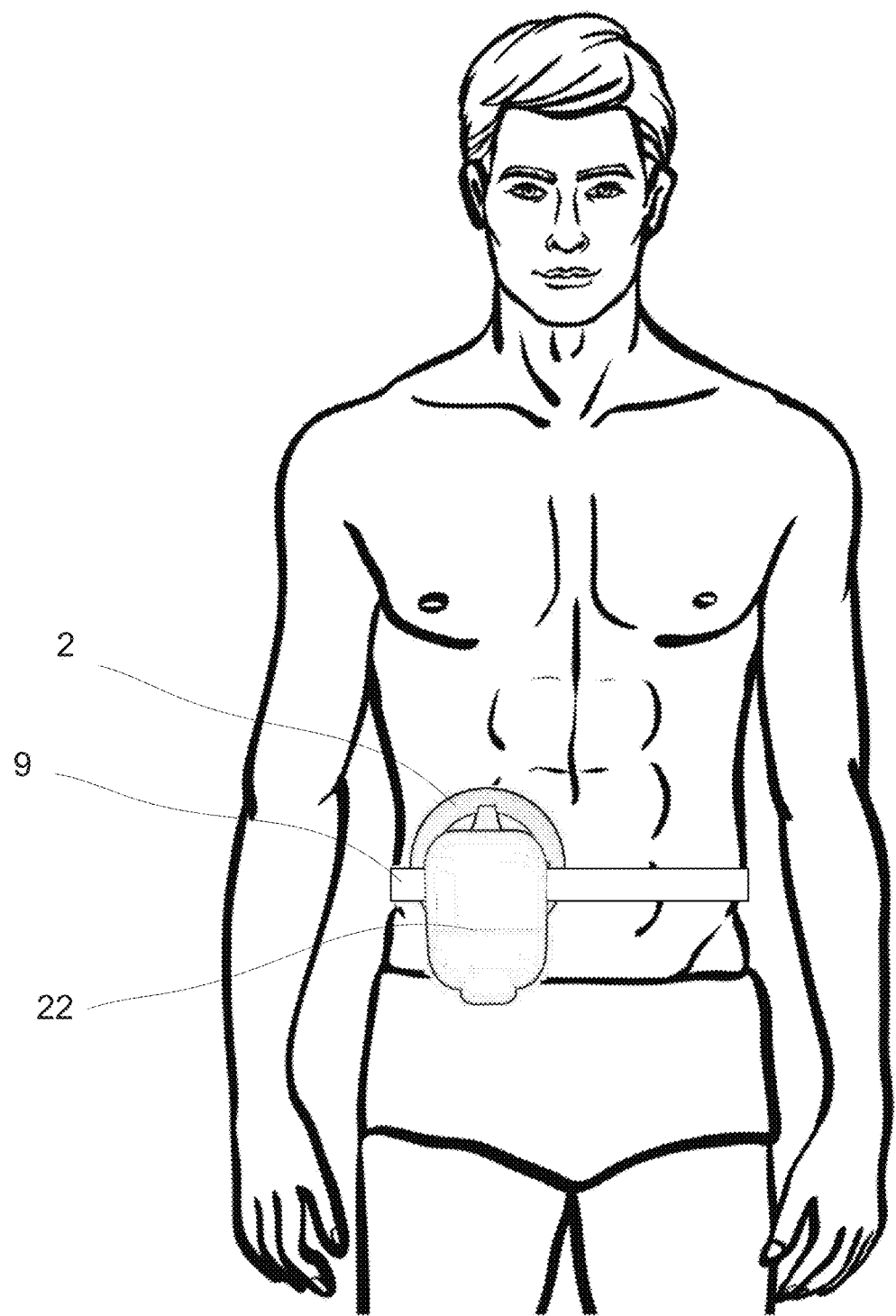

- Fig. 9 -
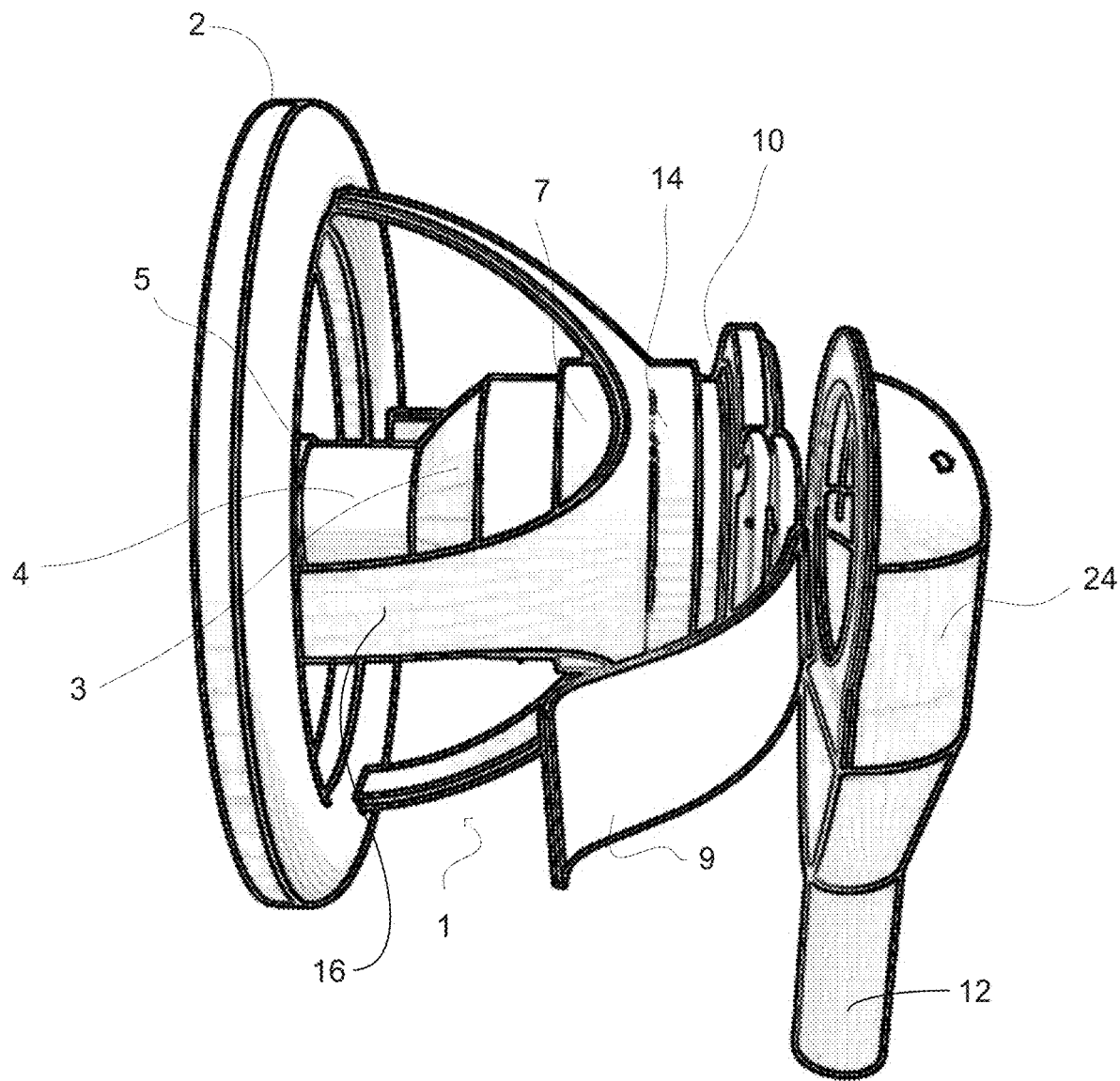

- Fig. 10 -
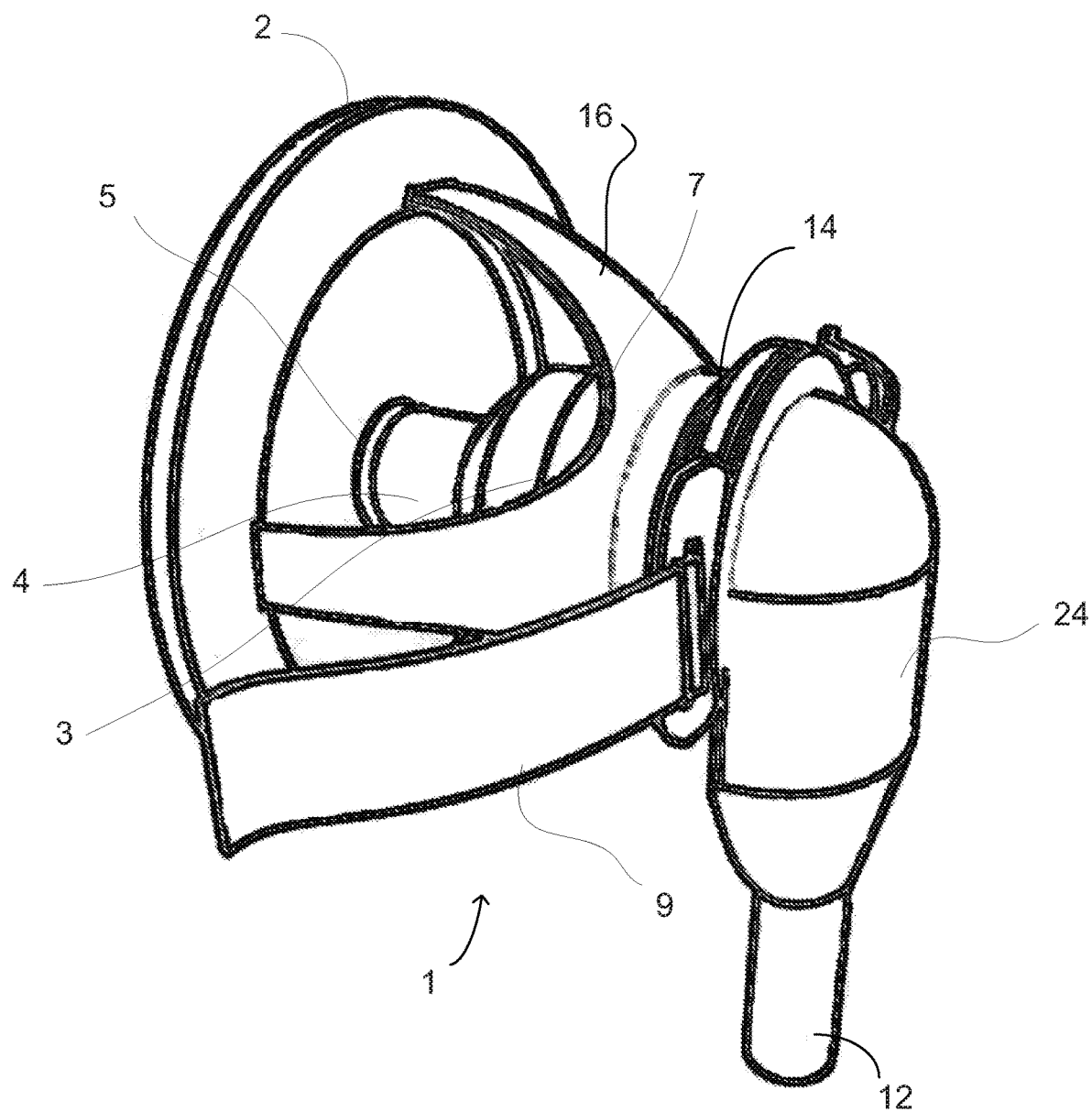

- Fig. 11 -
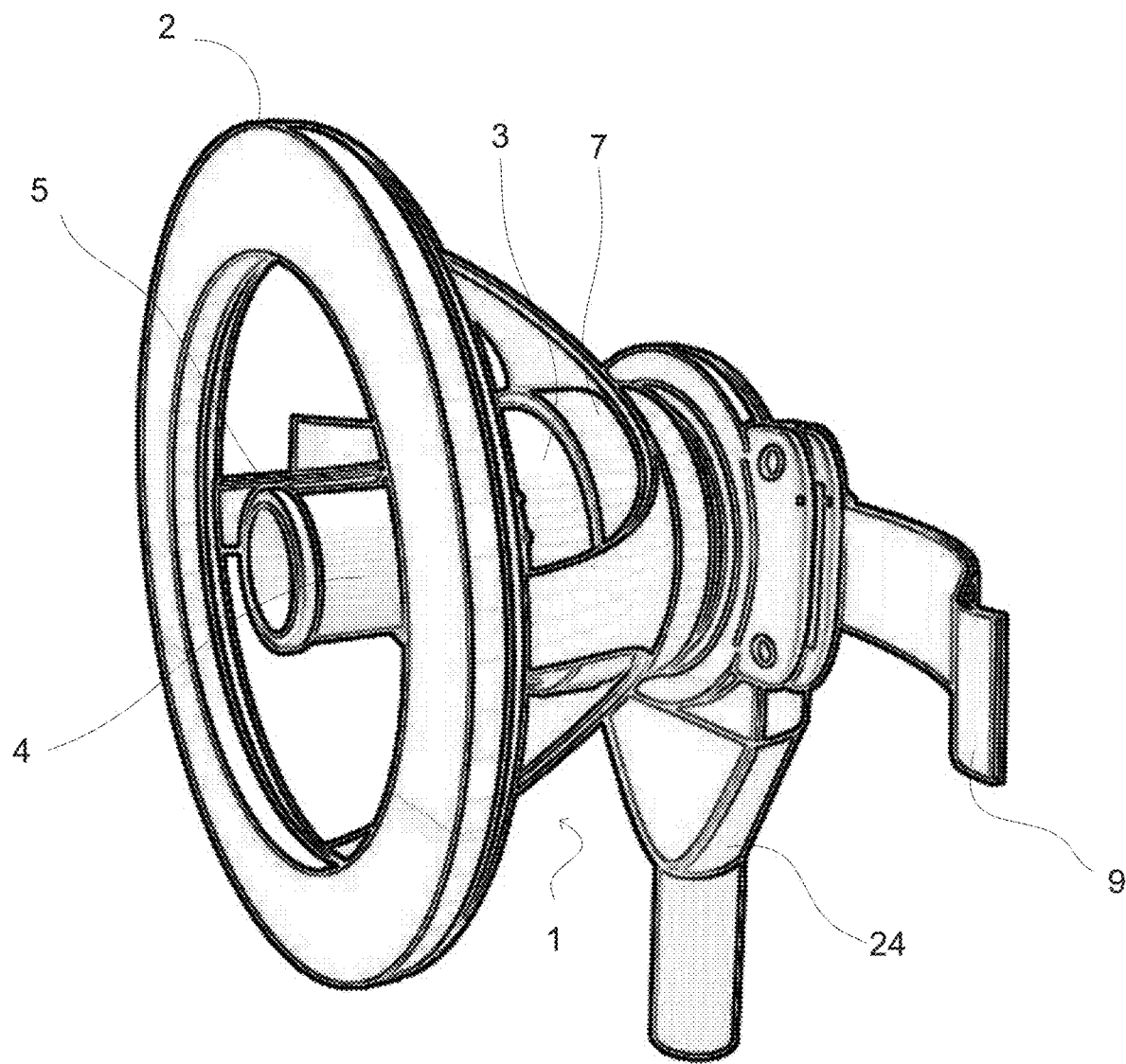

- Fig. 12 -
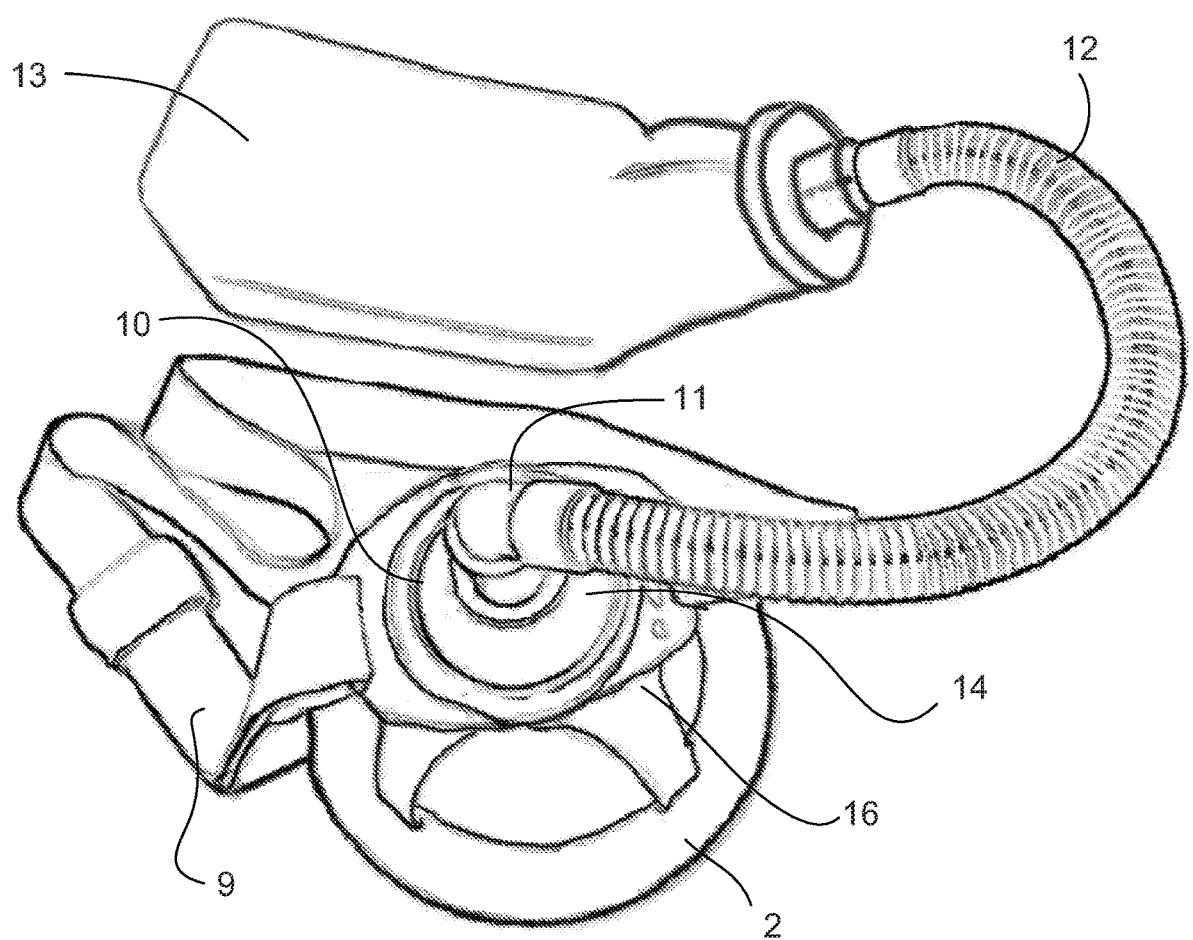

OSTOMY STOMA OUTPUT DIVERSION DEVICE

FIELD OF THE INVENTION

The present invention relates to a medical device designed to capture ostomy effluent output without the need of an adhesive-based ostomy pouching system, allowing extended periods of time without skin being covered, and designed to improve chronic peristomal skin conditions.

BACKGROUND OF THE INVENTION

Surgical procedures such as a colostomy, urostomy and ileostomy involve rerouting of the colon or ureter so that effluent can be discharged through an artificial opening formed in the ostomy patient's (also referred to herein as ostomate) body. This artificial opening, called a stoma, is typically located in the abdomen and may be about 0.5 to 2.5 inches or more in diameter.

The new artificial opening, or stoma, made on the abdominal wall, has no voluntary sphincter control by the ostomate. Collection of involuntary waste seepage is by a pouching system, typically comprising a pouch and baseplate, or other receptacle attached to the ostomate's body, where the pouching system is disposed of after use, and replaced with a fresh pouching system. Typically, such pouching systems are attached to the body over the stoma by means of a baseplate with adhesive backing which must be positioned over the stoma with precision to achieve a reliable attachment and seal. It is essential that this baseplate be mounted directly and concentrically over the stoma and further, that it be tightly secured to the body, otherwise leakage of waste onto the surrounding skin area can occur.

The pouching system is typically replaced every 2 to 5 days, with the replacement process typically taking 15 to 30 minutes. During the pouching system replacement process, while the pouching system is removed and the peristomal skin is exposed, the common practice has been to first clean and dry the peristomal skin, then treat and medicate any skin irregularities, followed by thorough drying of the skin and application of the new pouching system. Continued seepage of effluent and other uncontrollable factors, often cause the ostomate to hasten the process and apply the new pouching system prematurely, leading to further exacerbation of any emerging or existing skin conditions. Patients often experience acute or chronic peristomal skin conditions caused by medical adhesive related skin injury, moisture associated skin damage, allergic reactions to ostomy supply materials, and extended wear times with limited time to adequately treat skin before applying the new pouching system.

Attempts have been made to improve the procedures mentioned above for replacing pouches and cleaning the stoma and surrounding areas. The following references represent some of these past attempts, and each of the documents cited below are hereby expressly incorporated herein by reference, in their entireties:

WIPO Patent Publication Number WO2001000260 Colostomy Pump Device

A device (10) for evacuating waste product through an orifice in a mammalian body, the device (10) including a chamber (11) having an irrigating means (16) for introducing an irrigating fluid into the orifice and a suction means (40) for removing the irrigating fluid and waste products from the orifice.

U.S. Application No. 20130180294 Ostomy Device Apparatus and System

Devices for insertion into a stoma formed in a patient's body are provided, comprising a tube having distal and proximal ends and defining a path for movement of waste. To retain the device in the stoma and seal the stoma, the tube includes a retention mechanism located on the distal end and/or a sealing mechanism extending along a length of the tube between the proximal and distal ends. Collection apparatus for collecting waste from a patient's body also are provided, comprising a waste pouch and a connector for connecting the collection apparatus to a device inserted into a stoma. Additionally, waste collection systems for collecting waste from a patient's body are provided, comprising a tube for insertion into a stoma and a waste pouch. Each system may comprise a separate tube and waste pouch or the tube and waste pouch may be formed as an integral, inseparable component.

Canadian Patent No. CN1074687406 Stoma Drainage Bag Support Frame

The invention provides a stoma drainage bag support frame. The support frame comprises a first annular bracket, a second annular bracket and connecting rods, the outer diameter of the second annular bracket is smaller than the inner diameter of an opening of a drainage bag, the number of the connecting rods is three, the connecting rods are evenly arranged on the first annular bracket and the second annular bracket and connect the first annular bracket with the second annular bracket, the vertical distance between the first annular bracket and the second annular bracket is 2-5 cm, and the second annular bracket is provided with three convex portions, wherein the three convex portions are arranged at the joints of the connecting rods and the second annular bracket, externally protrude in a same plane with the second annular bracket and are used for fixing the bracket in a base plate ring of the stoma drainage bag. The stoma drainage bag support frame is placed between a drainage base plate and the drainage bag, by means of the support frame, damage to or necroses of a gut or an external segment of a ureter under pressure caused by negative pressure generated by drainage is avoided, and meanwhile, the phenomenon of liquid backflow caused by negative pressure effect and infection of a patient are avoided, so that health of the patient is guaranteed.

Each of the devices and methods set forth above are useful, but these advancements also have disadvantages. It would be desirable, therefore, to provide an ostomy output diversion device that is simple to use, inexpensive to manufacture, and which provides a useful and efficient way to maintain the health and cleanliness of a patient's stoma and surrounding skin and tissue.

BRIEF SUMMARY OF THE INVENTION

The present invention relates to a medical device designed to capture ostomy effluent output without the need of an ostomy pouching system, allowing extended periods of time without skin being covered by an adhesive baseplate, and designed to improve chronic and acute peristomal skin conditions. In a first embodiment, the ostomy output diversion device includes a main body member, the outer frame of the main body member is shaped in a manner to extend away from the body, with space between the frame supports to allow open access to the peristomal skin, allowing patients to treat and medicate the peristomal skin, and to leave the skin uncovered for an extended period of time, an inner tube guide for aligning and supporting an inner tube, an inner tube member positioned through the center of the main body member and inner tube guide and adjustable to allow movement within the main body member and inner tube guide, a stoma-sized adapter attached to the bottom end of the inner tube member and sized to fit over the stoma, a sealing ring attached to the bottom of the stoma-sized adapter to prevent effluent from seeping between the adapter and adjacent skin, a pressure adjustment lock to apply adequate pressure between the stoma-sized adapter and the adjacent skin during application, an effluent draining tube attached to the drain tube connector on the distal end of the inner tube, the opposite end of the effluent draining tube leading to a reservoir container to contain effluent output, with an adjustable body support strap used to secure the device to the body during application.

DESCRIPTION OF THE DRAWINGS

These and other features, aspects, and advantages of the present invention will become better understood with regard to the following description and accompanying drawings where:

FIG. 1 is a perspective view of one embodiment of an ostomy output diversion device, including a main body member, attached to a base ring, and having an inner tube member positioned through the center of the main body member, inner tube guide, and a stoma-sized adapter, with a sealing ring attached, and an adjustable body support strap used to secure the device to the body;

FIG. 2 is a perspective view to illustrate one embodiment of the ostomy output diversion device strapped on a person in a typical manner, and a drain tube attached to a reservoir;

FIG. 3A is a perspective view of one embodiment of the ostomy output diversion device, and the removable strap and ring positioned on the device;

FIG. 3B is a perspective, exploded view of one embodiment of the ostomy output diversion device, wherein the strap ring and strap are removed from the outer frame;

FIGS. 4A and 4B is a perspective view of one embodiment of an ostomy output diversion device showing a body support strap used to secure the ostomy output diversion device to the body;

FIG. 5 is a perspective, exploded view of one embodiment of an ostomy output diversion device, wherein the strap ring and strap are removed from the outer frame, and further showing a pouch mounting ring on a distal portion of the strap ring for connection with an ostomy pouch;

FIG. 6 is a perspective view of the embodiment of an ostomy output diversion device shown in FIG. 5, wherein the strap ring is secured over the outer frame, and the ostomy pouch is connected to the pouch mounting ring;

FIG. 7 is a perspective view of the embodiment of an ostomy output diversion device shown in FIG. 5, wherein the strap ring is secured over the outer frame, and the ostomy pouch is connected to the pouch mounting ring;

FIG. 8 is a perspective view of the embodiment of an ostomy output diversion device shown in FIG. 5, wherein the strap ring is secured over the outer frame, and the ostomy pouch is connected to the pouch mounting ring, and wherein the apparatus is strapped onto a patient's body;

FIG. 9 is a perspective, exploded view of one embodiment of an ostomy output diversion device, wherein the strap ring is removably secured over the outer frame, and wherein an output adapter is attachable to the strap ring;

FIG. 10 is a perspective view of one embodiment of an ostomy output diversion device, wherein the strap ring is removably secured over the outer frame, and wherein an output adapter is removably attached to the strap ring;

FIG. 11 is a perspective view of one embodiment of an ostomy output diversion device, wherein the strap ring is removably secured over the outer frame, and wherein an output adapter is removably attached to the strap ring; and FIG. 12 is a perspective view of one embodiment of an ostomy output diversion device, including a main body member attached to a base ring, and having an inner tube member positioned through the center of the main body member, inner tube guide, and a stoma-sized adapter with a sealing ring attached thereto, and an adjustable body support strap used to secure the device to the body, and further including an elbow member attached to a drain tube connector, and a drainage tube extending between the elbow member and a reservoir for receiving effluent.

DETAILED DESCRIPTION OF THE INVENTION

FIG. 1 illustrates an embodiment of the present invention whereby the ostomy output diversion device includes a main body member 1 having a base ring 2, support members 16 attached to the base ring 2 on a first end thereof, and an outer frame 14 attached to the support members 16 on a second end thereof. In a preferred embodiment, the outer frame 14 extends away from the patient's body, with space provided between support members 16 to allow open access to the peristomal skin. The base ring 2 may be constructed of any suitable material, but preferably of soft material for skin contact comfort. In one embodiment, the base ring 2 may be malleable, so that a patient may form the base ring 2 into any desired shape or configuration to conform to the contour of his or her abdominal shape, as desired, for ease of use. In this embodiment, the base ring 2 may be made from flexible materials, such as rubber, foam, or other suitable formable materials, and may also include a structural wire to allow the base ring to maintain the desired configuration formed by the patient. In some embodiments, the base ring 2 may be removable and replaceable with base rings of other sizes, shapes, or configurations.

In a preferred embodiment, the ostomy diversion device further includes a centrally located inner tube member 3, positioned through the center of the main body member 1 and an inner tube guide 7 that is held in place by support spokes 15 that are attached to the inner portion of the support members 16. A stoma-sized adapter 4 is attached to the proximal end of the inner tube member 3 and sized to fit over the stoma, and the adapter 4 includes a sealing ring 5 that is used to prevent effluent from seeping between the stoma-sized adapter 4 and adjacent skin. The inner tube member 3 is preferably telescopic in nature, and is incrementally or infinitely adjustable inwardly and outwardly in linear fashion, in order to allow movement within the main body member 1. A pressure adjustment lock 6 is used to apply and maintain adequate pressure between the stoma-sized adapter 4 and the adjacent skin during application. In use, when the base ring is placed in the proper position against a patient's skin, the inner tube member 3 may be extended toward the stoma to ensure a tight fit, and the pressure adjustment lock 6 is used to maintain the extended position thereof. The pressure adjustment lock 6 may be disengaged and repositioned during use, or after use, as desired.

In a preferred embodiment, the ostomy output diversion device includes a removable body support strap 9 and strap mounting ring 10, used to secure the ostomy output diversion device to the body during application. The removable body support strap 9 may be affixed to the strap mounting ring 10, which fits over or onto the distal portion of the outer frame member 14, as shown in FIGS. 3A and 3B, or the strap 9 may be affixed to other portions of the device, such as the base ring 2 as shown in FIG. 4. Any suitable strap means may be used to attach the device to a patient's body, so long as the device, and specifically the sealing ring 5 of the stoma-sized adapter 4 are held firmly in place against the patient's skin, in order to prevent any effluent from leaking therefrom.

In a preferred embodiment, the ostomy output diversion device includes a drain tube connector 8, used to connect a drain tube 12 to the distal end of the inner tube 3, and to a reservoir 13 to collect ostomy output. Essentially, a clear drainage passage is formed from the adapter 4 through the inner tube 3, the tube connector 8, and into the drain tube 12, so that effluent may pass unobstructed from the stoma to the reservoir 13 without leakage from any point along the way. In a preferred embodiment, a hollow elbow joint 12 may be affixed to the tube connector 8 on a first side thereof, and the second side of the elbow member 11 may be attached to the drainage tube 12 leading to the reservoir 13, as shown in FIG. 12. The elbow joint 11 may be formed into any desired angle, and preferably is formed into an angle in the range of 40 to 50 degrees. This arrangement allows the drainage tube 12 to extend in any desired direction toward the reservoir 13 in a low profile manner, rather than having the drainage tube 12 extend in linear fashion from the tube connector 8, which may be awkward or cumbersome in some situations or tight spaces.

FIG. 2 illustrates an embodiment of the present invention whereby the ostomy output diversion device is strapped on a person in a typical manner, covering and sealing over the person's stoma, allowing effluent to exit the stoma, pass through the ostomy output diversion device, into a drain tube 12 attached to the drain tube connector 8 of the ostomy output device, and into a reservoir 13 for collecting ostomy output.

FIG. 3A illustrates an embodiment of the present invention whereby the ostomy output diversion device has a body support strap 9 and strap mounting ring 10 that fits over the distal end of the outer frame 14, so that the strap is used to secure the ostomy output diversion device to the body during application. FIG. 3B illustrates an embodiment of the present invention whereby the body support strap 9 and strap mounting ring 10 are removable from the ostomy diversion device.

FIG. 4 illustrates an embodiment of the present invention whereby the body support strap 9 is integrally formed with the base ring 2 for securing the ostomy output diversion device to the body during application.

In use, after an ostomy patient has removed a used bag and attachment apparatus and cleaned the skin around the stoma, the patient places the base ring 2 firmly against his skin so that the adapter 4 is positioned over the stoma. The patient then extends the adapter 4 inwardly toward the stoma until the sealing ring 5 is firmly in place around the stoma and secured in place by the pressure adjustment lock 6, and then affixes the strap ring 10 around the distal portion of the outer frame 14 and secures the strap 9 around his body. The next step includes affixing the drainage tube 12 to the tube connector 8 (or affixing the drainage tube to the elbow joint 11, and the other side of the elbow joint 11 to the tube connector 8), and connects the other end of the drainage tube 12 to a reservoir 13. It should be understood that some of these steps may be combined or performed out of the recited order without departing from the scope or the spirit of the present invention.

This device allows the peristomal skin around the stoma to remain uncovered for extended periods of time, so that it can breathe and potentially be treated with an ointment, salve or other topical medical treatment, for as long as the patient desires. Once the ostomy output diversion device is properly secured to the patient's body, the patient's hands can remain free of the device, and may be used for other tasks or activities (or may simply rest) while the device is held in place by the straps 9.

FIGS. 5-8 show another embodiment of the present invention, wherein the strap ring 10 includes a pouch mounting ring 20 on an outer portion thereof. An ostomy pouch 22 may be removably attached to the pouch ring 20 in order to receive effluent from the patient's stoma while the ostomy output diversion device is properly secured to a patient's body.

FIGS. 9-11 illustrate another embodiment of the present invention, wherein an output adapter 24 may be removably secured to the strap ring 10 (or, alternatively, to a pouch mounting ring 20). The output adapter 24 is attached to a drainage tube, which in turn is operatively attached to a reservoir for receiving effluent from the patient's stoma.

In another alternate embodiment, the inner tube member may be removable and interchangeable with a disposable cartridge or receptacle, such as a receptacle as described in U.S. Pat. No. 10,130,505, which is hereby incorporated herein by reference, in its entirety. In this embodiment, the disposable receptacle may be inserted into the outer frame member and used to receive the effluent from the stoma while the ostomy output diversion device is in place on a patient's body. Then, the disposable receptacle containing the effluent may be removed, sealed, and properly disposed of.

It should be understood that other structural arrangements may be used without departing from the spirit or scope of the present invention. For instance, it is conceived that one or two support members may be used, rather than the three support members shown in the Figures, in order to provide easier access to the peristomal skin while the ostomy output diversion device is strapped onto a patient's body.

Although the present invention has been described in considerable detail with reference to certain preferred versions thereof, other versions are possible. Therefore, the spirit and scope of the appended claims should not be limited to the description of the preferred versions contained herein. All features disclosed in this specification may be replaced by alternative features serving the same, equivalent or similar purpose, unless expressly stated otherwise. Thus, unless expressly stated otherwise, each feature disclosed is one example only of a generic series of equivalent or similar features.

What is claimed:

1. An ostomy output diversion device comprising;
 a base ring including a top surface and a bottom surface, wherein said bottom surface is used for placement against a user's skin around a stoma and peristomal skin during use of said output diversion device;
 an outer frame member attached to at least one support member extending from said top surface of said base ring, wherein said at least one support member provides an opening between said base ring and said outer frame member to provide access to peristomal skin around said stoma for application of ointments and medications while said base ring is positioned against said user's skin around said stoma and peristomal skin; and an adapter for receiving effluent discharged from said stoma, said adapter attached to said outer frame member, wherein said adapter includes a first opening for drainage, and a second opening that is sized to surround a periphery of said stoma.

2. The ostomy output diversion device set forth in claim 1, wherein said adapter is adjustable in linear fashion inwardly toward said base ring and outwardly toward an apex of said outer frame.

3. The ostomy output diversion device set forth in claim 2, wherein said adjustable adapter includes a pressure adjustment lock in order to secure said adjustable adapter in a desired extended or retracted position.

4. The ostomy output diversion device set forth in claim 1, further including a strap member that is connected to said base ring, wherein said strap member may be secured around a user's body in order to hold said ostomy output diversion device against said user's body.

5. The ostomy output diversion device set forth in claim 1, further including a strap member attached to a strap ring, wherein said strap ring is removably fitted over said outer frame member, and said strap member configured to be secured around a user's body in order to hold said ostomy output diversion device against said user's body.

6. The ostomy output diversion device set forth in claim 5, wherein said strap ring includes a pouch mounting ring on one side thereof for removably receiving an ostomy pouch.

7. The ostomy output diversion device set forth in claim 6, further including an ostomy pouch that is removably attachable to said pouch mounting ring.

8. The ostomy output diversion device set forth in claim 6, further including an output adapter that is connected to said pouch mounting ring, and is further connected to said first end of said drainage tube.

9. The ostomy output diversion device set forth in claim 1, wherein said base ring is constructed of a flexible material to conform to various body contours.

10. The ostomy output diversion device set forth in claim 1, further including a drainage tube having a first and second end, said first end of said drainage tube being operatively attached to said first opening in said adapter and said second end of said drainage tube being connected to a reservoir for receiving and collecting effluent.

* * * * *